United States Patent [19]
Takeuchi

[11] Patent Number: 4,537,453
[45] Date of Patent: Aug. 27, 1985

[54] CONNECTING MECHANISM OF LIGHT SOURCE DEVICE FOR ENDOSCOPE
[75] Inventor: Haruo Takeuchi, Tokyo, Japan
[73] Assignee: Olympus Optical Co., Ltd., Tokyo, Japan
[21] Appl. No.: 631,824
[22] Filed: Jul. 17, 1984
[30] Foreign Application Priority Data
Jul. 19, 1983 [JP] Japan ................................. 58-130153
[51] Int. Cl.³ .......................................... H01R 27/00
[52] U.S. Cl. .................................... 339/33; 339/16 R
[58] Field of Search ...................... 339/15, 16 R, 16 C, 339/16 RC, 31 R, 31 B, 31 L, 31 M, 31 T, 32 R, 32 M, 33; 128/4, 6; 362/32, 226

[56] References Cited
U.S. PATENT DOCUMENTS

| | | | |
|---|---|---|---|
| 2,848,701 | 8/1958 | McKee et al. | 339/33 |
| 2,912,665 | 11/1959 | Irwin | 339/33 |
| 2,976,511 | 3/1961 | Lipsitz | 339/33 |
| 2,982,936 | 5/1961 | Pennock, Jr. et al. | 339/33 |
| 3,067,399 | 12/1962 | Matsui | 339/33 |
| 4,245,875 | 1/1981 | Shaffer et al. | 339/32 R |
| 4,414,608 | 11/1983 | Furihata | 362/32 |

FOREIGN PATENT DOCUMENTS
57-39014  3/1982  Japan .

Primary Examiner—John McQuade

[57] ABSTRACT

A connecting mechanism has a cylindrical socket mounted on a light source device, and a cylindrical member fitted to the outside of the socket. The member is engaged with a first type of connector to hold it when the connector is connected to the socket. A slide ring is arranged opposite to the cylindrical member to be movable between a normal position and an evacuating position. In a normal position, the slide ring is engaged with a second type of connector of an endoscope to hold it when the second type connector is connected the socket. When a third type of connector is to be connected to the socket, the slide ring is in contact with the third type of connector and moved from the normal position to the evacuating position by the third type connector, thereby allowing the third type connector to be connected to the socket.

13 Claims, 7 Drawing Figures

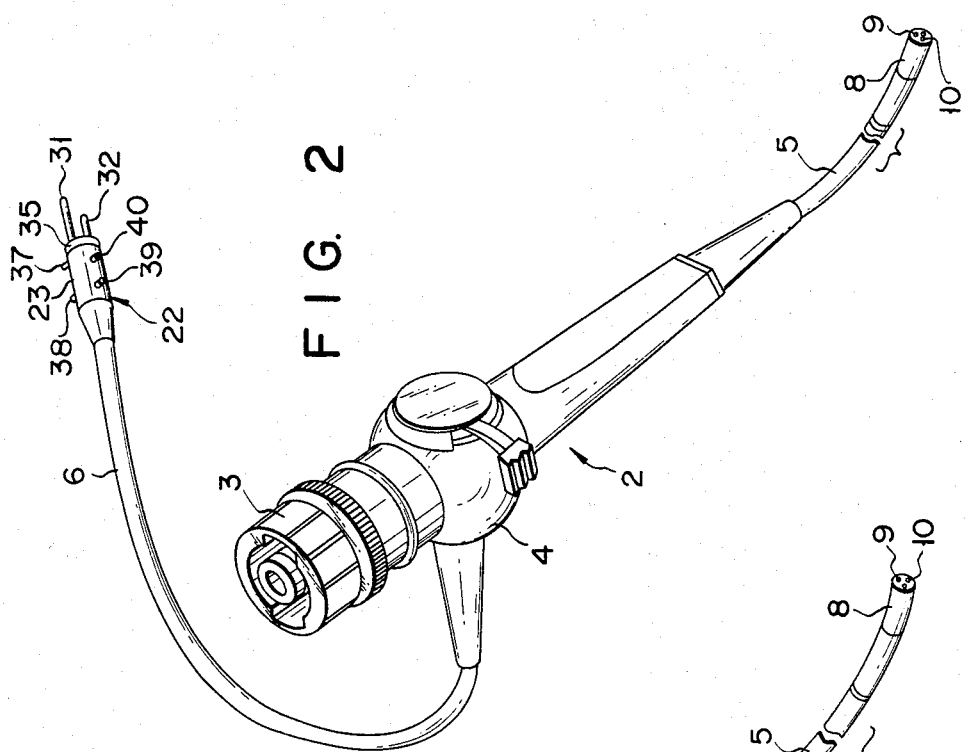
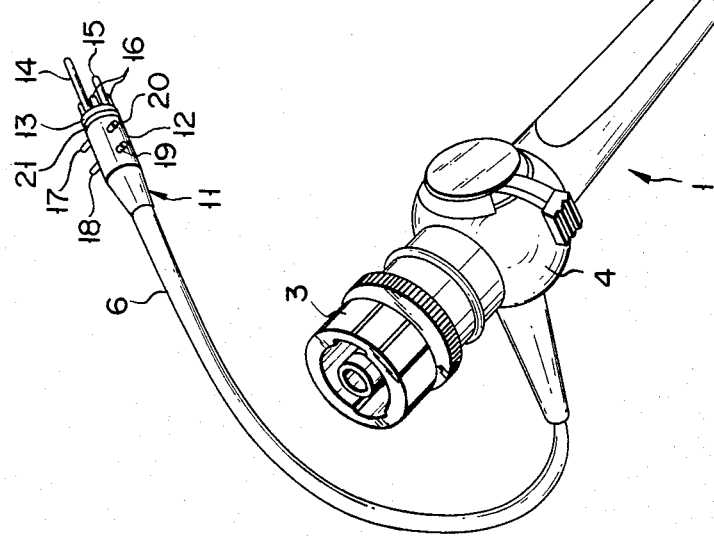

4,537,453

CONNECTING MECHANISM OF LIGHT SOURCE DEVICE FOR ENDOSCOPE

BACKGROUND OF THE INVENTION

The present invention relates to a connecting mechanism of a light source device for an endoscope, to which a connector of the endoscope is connected.

A light source device for an endoscope generally has a socket as a connecting mechanism, and a connector mounted at the end of the cable of the endoscope is connected to the socket. When the connector is connected to the socket, an electrical system, an optical system and a gas and water feeding system of the endoscope are respectively connected to those of the light source device.

The connector of the endoscope has a light guide tube, a gas feeding tube and a plurality of contact pins, which are projected from the bottom surface of a recess portion formed at the end face of a connector body. In other words, at least the base ends of the light guide tube, the gas feeding tube and the contact pins are enclosed by an engaging column defining the recess portion.

As an endoscope cleaning technique has recently made progress, the entire endoscope has been formed in a waterproof structure for its disinfection and irrigation. Since the recess portion is formed at the end of the connector body, as described above, and since the light guide tube, the gas feeding tube and the contact pins are projected in the recess portion, detergent remains, even if the endoscope is taken out of a detergent tank, in the gaps between the tubes and between the pins in the bottom of the recess portion, and such detergent cannot be wiped off.

Another connector has been proposed in which the entire structure has been altered: the end of the connector body is formed in a flat surface, a light guide tube and a gas feeding tube are projected from the flat surface, and a plurality of contacts are protruded on the outer peripheral surface of the body. Since the connector of this type does not have a recess portion on the outer surface of the body, detergent adhered to the surface of the connector body can be naturally wiped off after an irrigation, and even if the detergent remains on the outer surface of the connector body, the detergent can be readily wiped off.

When an endoscope having a connector which has an entirely altered structure as described above is used, the structure of the socket of a light source device should also be changed to match the connector. However, the light source device is expensive, and accordingly, it is not economical for users to prepare a plurality of light source devices with different sockets for the altered connectors.

From the above described facts, a connection system has been proposed which is capable of being used for the light source device of any type of socket, and which has obtained interchangeability between the connectors of different types and the light source device by employing two types of adapters between the connector of the endoscope and the socket of the light source device. However, the recent endoscope tends to use a multiplex transmission sytem for transmitting a number of signals by utilizing less signal lines. There arises a matching problem when the same photoelectric source device is used for both the endoscope which employs the above-described transmission system and the endoscope of the conventional type. Thus, in the proposed endoscope, an adapter for a light source device side and an adapter for a connector side are prepared to allow the matching therebetween, an electric system is associated therewith, and the necessary electric processing is executed. In other words, two types of adapters are used to match the endoscopes of different types. When two such adapters are thus used, it is disadvantageous that the structure becomes complicated and expensive, and the handling also becomes complicated.

Further, in order to reproduce individual signals from a plurality of superposed signals, the signals are fed through the both adapters. Thus, the signals should twice pass through the contacts of a contacting type, thereby disadvantageously deteriorating the reliability.

Then, a connecting mechanism is proposed which is capable of simply connecting the connectors of different types of endoscopes, without using the adapters of other members, by providing a plurality of engaging stationary units for fixedly positioning the connectors to be connected corresponding to the different types of connectors in a socket.

However, the connecting mechanism of this type is constructed to connect a variety of connectors by utilizing the difference of the inner diameters between the engaging stationary units. Therefore, even if there is an engaging stationary unit adapted for a special connector, the special connector makes contact with another engaging stationary unit, not used at that time, with the result that the connector cannot be plugged in. In other words, when using the endoscope having this special connector, it has the drawback that the adapters should still be used.

SUMMARY OF THE INVENTION

The present invention has been made in consideration of this and has for its object to provide a connecting mechanism of a light source device for an endoscope which is capable of simply connecting the connectors for the endoscopes of different types without using adapters of other members and increasing the range of the endoscope to be applied.

According to an aspect of the invention, there is provided a connecting mechanism of a light source device for an endoscope which comprises a socket to which light guide tubes and electric contacts of connectors of various types; a first holding unit adapted to engage with a cylindrical connector body of the connector for holding the connector body when the connector of first type is connected to the socket; and a second holding unit adapted to engage with a connector body of a connector of second type to hold the connector body when the connector of the second type, which has a cylindrical connector body with an outer diameter larger than that of the connector body of the above first type, is connected to the socket. The second holding unit is moved to an evacuating position to allow the connector of third type to be connected to the socket upon pressing the connector body when the connector of the third type, having the cylindrical connector body with an outer diameter larger than that of the connector body of the second type, is connected to the socket.

According to the above-described connecting mechanism, connectors of various types can be connected to the socket of one type without utilizing an adapter of other member. Therefore, complicated operations such as selection and use of the adapters can be eliminated, and the connectors of various types can be readily connected to a light source device.

BRIEF DESCRIPTION OF THE DRAWINGS

FIGS. 1 and 2 are perspective views showing endoscopes having connectors of different types.

FIGS. 4 to 7 show a connecting mechanism of a light source device for an endoscope according to an embodiment of the present invention, in which FIG. 4 is a perspective view of the connecting mechanism, FIG. 5 is a sectional view of the connecting mechanism, FIG. 6 is a front view partly deleted showing the connecting mechanism, and FIG. 7 is a view schematically showing a guide groove and a locking groove.

DETAILED DESCRIPTION OF THE PREFERRED EMBODIMENT

Figure 3:
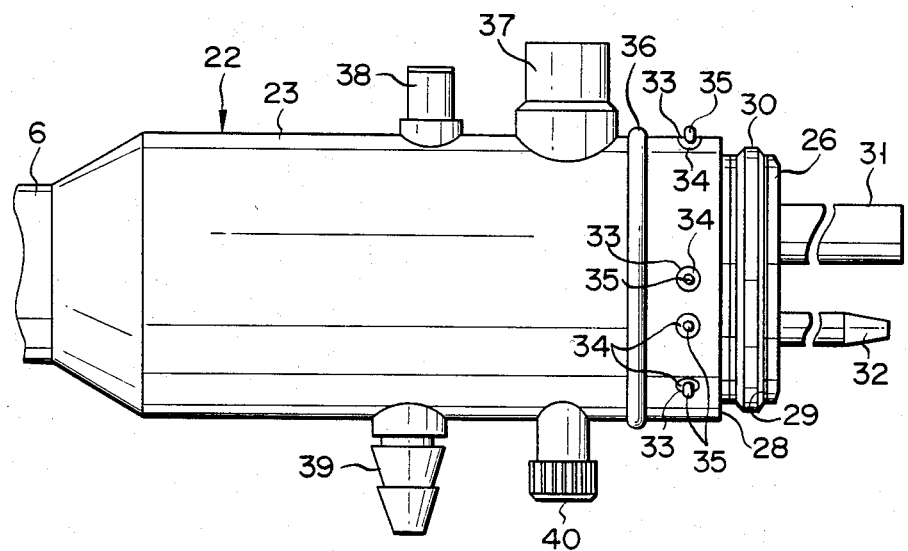
FIG. 3 is a side view showing one of the connectors.

The present invention will now be described in more detail with reference to the accompanying drawings.

FIG. 1 shows an endoscope 1 having a connector 11 of the type heretofore widely used (hereafter referred to as "the first type" of connector), and FIG. 2 shows an endoscope 2 having a connector 22 of a novel type (hereafter referred to as "the second type" of connector). These endoscopes 1 and 2 have the same fundamental structure except for connectors and electrical systems to be described later. In both the endoscopes 1 and 2, a flexible and long insert section 5 and a light guide cable 6 are connected to an operation section 4 which has an eyepiece unit 3. A light guide (not shown), formed of an optical fiber bundle, is inserted into the cable 6. The light guide is connected to an illumination window 9 of the end unit 8 of the insert section 5 through the operation section 4 and the interior of the insert section 5. An image guide (not shown), connected at its one end to the eyepiece unit 3 and connected at the other end to an observation window 10 of the end unit 8, is inserted into the insert section 5.

The connector 11 of the first type is mounted at the end of the cable 6 of the endoscope 1. A connector body 12 of the connector 11 is formed in a cylindrical shape. At the distal end of the body 12 is mounted an engaging cylinder 13 which defines a recess portion. From the inner bottom of the recess portion surrounded by the cylinder 13 are projected a light guide tube 14 having the light guide therein, an air feeding tube 15 and a plurality of contact pins 16 along the axial direction of the body 12. Further, from the outer peripheral surface of the body 12 are projected an air and water feeding mouthpiece 17, a carbon dioxide gas feeding mouthpiece 18, a suction mouthpiece 19 and a high frequency earth mouthpiece 20. An engaging ring 21 is fitted to the outer peripheral surface of the end of the body 12.

The connector 22 of the second type, mounted at the end of the cable 6 of the endoscope 2, is constructed as shown in FIG. 3. More particularly, the connector 22 has a connector body 23 which is formed in a cylindrical shape having an outer diameter larger than the body 12 of the connector 11 of the first type. This body 23 is connected at its one end to the cable 6. An end plate 26 is fixed to the other end of the body 23 to close the other end. Thus, this end plate 26 is formed to have a diameter slightly smaller than the body 23, and a stepped part 28 is formed at the connecting portion between the body 23 and end plate. An annular groove 29 having a U-shaped cross section is formed on the outer peripheral surface of the plate 26, and an engaging ring 30, formed of an elastic engaging member such as, for example, an NBR rubber, or a C-shaped ring metal spring, is engaged with in the groove 29. From the plate 26 are forwardly projected a light guide tube 31 having a light guide and an air feeding tube 32 along the axial direction of the connector body 23. Further, a plurality of through holes 33 are opened at a predetermined circumferential interval on the outer peripheral surface at the end side of the body 23, and a plurality of contact pins 35 are secured through an insulating bush 34 to the respective holes 33. The pins 35 are respectively projected at their ends from the outer peripheral surface of the body 23, and are electrically connected at their ends to an endoscope camera through a signal line (not shown) inserted into the endoscope 2 to transmit and receive a photographing drive signal and a control signal. An annular projection 36 is integrally formed along the circumferential direction at the outer peripheral surface of the body 23, and is disposed slightly at the rear of the pins 35. The projecting height of the projection 36 is slightly higher than the projecting height of the pin 35. In this manner, even if the connector 22 is laid on a desk or the like, the pins 35 do not contact with the desk surface, thereby protecting the pins 35.

On the outer peripheral surface of the body 23 are projected, as shown in FIG. 3, an air and water feeding mouthpiece 37, a carbon dioxide gas feeding mouthpiece 38, a suction mouthpiece 39 and a high frequency earth mouthpiece 40.

Figure 4:
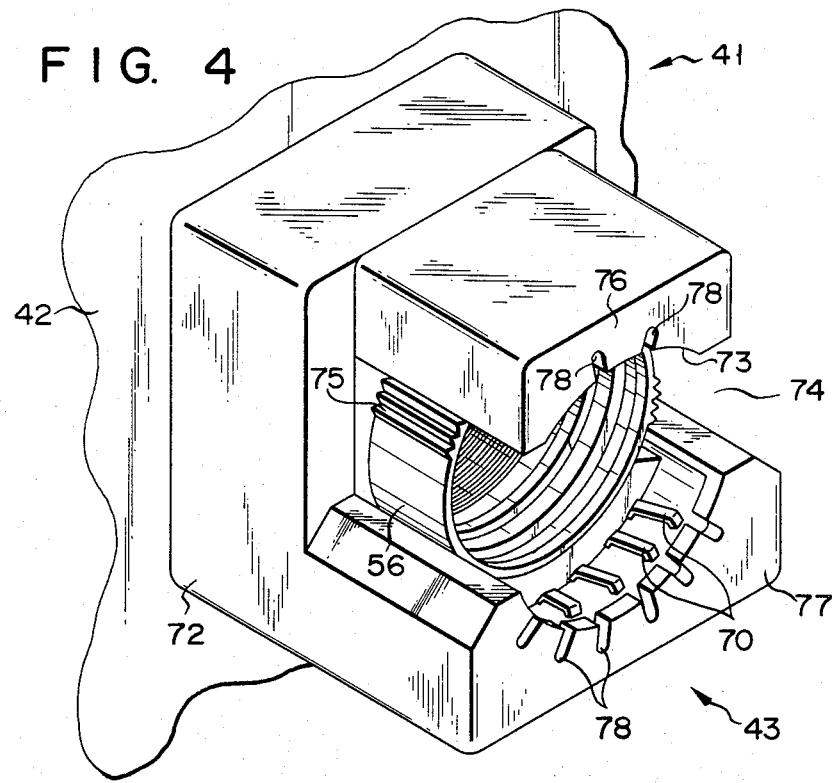
Figure 5:
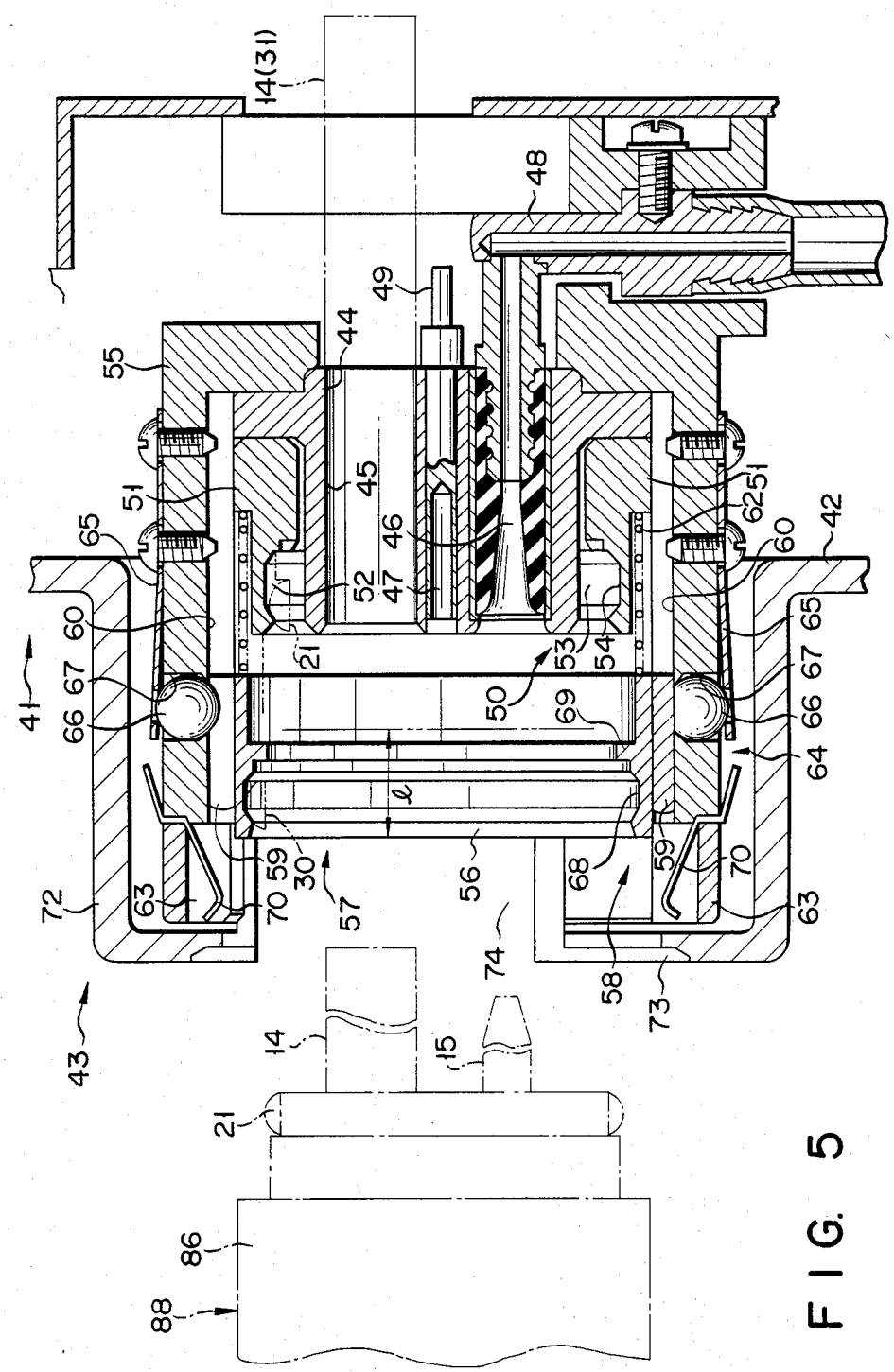

On the other hand, in FIGS. 4 and 5, reference numeral 41 designates a light source device. On the front panel 42 of the light source device 41 are provided a connecting mechanism 43, to which the connectors 11, 22 of the endoscopes 1, 2 are respectively connected. The connecting mechanism 43 has a socket 44 fastened to the front panel 42. This socket 44 is formed substantially in a cylindrical shape, and the front end face of the socket 44 is forwardly projected from the front panel 42. Further, a light guide tube inserting hole 45, an air feeding tube inserting hole 46 and a plurality of contact pin inserting holes 47 are formed in the socket 44 in parallel with the inserting direction of the connectors 11, 22, i.e., the axial direction of the socket. A light source lamp (not shown) is mounted opposite to the inserting hole 45 in the body of the light source device 41. An air feeding pipe 48 is provided in the inserting hole 46, and first electric connection terminals 49 are provided in the inserting holes 47.

The connecting mechanism 43 has a cylindrical member 51 as first holding means 50 for fixedly positioning and holding the connector 11 of the first type of the endoscope connected to the socket 44 at a predetermined position. This member 51 is fitted on the outer periphery of the socket 44. The member 51 has an annular recess 52 formed on the inner peripheral surface of the front end portion thereof, and an annular engaging gap 53 is defined by the recess 52 and the outer periphery of the front end portion of the socket 44. When the connector 11 of the first type is connected to the socket 44, the front end of the engaging cylinder 13 of the connector 11 is inserted into the gap 53. An engaging groove 54, to be engaged with the elastic engaging ring 21 of the connector 11 of the endoscope 1, is formed annularly on the inner periphery of the cylindrical member 51 opposed to the outer periphery of the front end of the socket 44 and hence on the inner surface of the recess 52.

Figure 7:
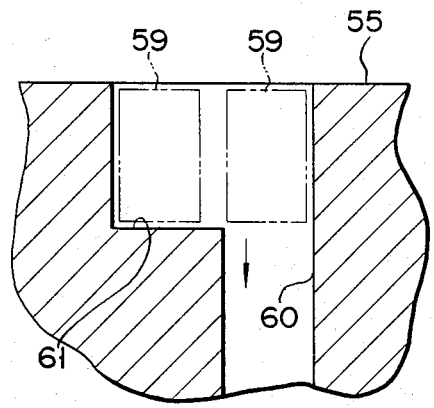

The socket 44 is supported by a supporting frame 55 of a substantially cylindrical shape which is fastened to the light source device 41. This frame 55 is disposed coaxially with the socket outside the socket 44 and extends over the front end of the socket 44. In the frame 55, an annular slide ring 56 is coaxially arranged with the socket 44 at a forward position from the socket 44. This slide ring 56 has an inner diameter substantially equal to the outer diameter of the body 23 of the second type of connector 22 to form second holding means 57 for fixedly positioning the connector 21 at a predetermined position. This slide ring 56 is inserted in the frame 55 to be movable between the normal position shown in FIG. 5 and an evacuating position adjacent to the socket 44 along the axial direction of the supporting frame. The slide ring 56 is also arranged to be rotatable around the axis thereof. The slide ring 56 is further specified in the movements by defining means 58 to be described as below. More specifically, a pair of projections 59 are formed at an angular interval of 180° on the outer periphery of the slide ring 56, and are respectively inserted into a pair of guide grooves 60 formed on the inner peripheral surface of the frame 55. These guide grooves 60 are axially formed in the length of the frame 55, as shown in FIG. 7, to guide the projections 59 along the guide grooves 60, thereby axially moving the slide ring 56. Further, locking grooves 61 are formed on the inner peripheral surface of the outer end of the frame 55 to continue to the guide grooves 60 and to extend circumferentially from the guide grooves 60, as shown in FIG. 7. When the slide ring 56 is rotated to engage the projections 59 with the locking grooves 61, the slide ring 56 is prevented from axial moving, thereby being held at the normal position.

The above-described slide ring 56 is elastically urged outwardly by a coiled spring 62 as an elastic member interposed between the cylindrical member 51 and the ring 56. The slide ring 56 is restricted to move forward in contact with a contact frame 63 provided on the front end of the supporting frame 55. When the projections 59 are located in the guide grooves 60, the slide ring 56 may be pushed into supporting frame 55 against the urging force of the spring 62. When the projections 59 are engaged into the locking grooves 61, the slide ring 56 cannot be inserted as described above. The projections 59 are positioned in any of the guide grooves 60 and the locking grooves 61 by a clicking mechanism 64. This clicking mechanism 64 has a pair of leaf springs 65, mounted on the outer surface of the frame 55, and a pair of click balls 66, respectively engaged with the leaf springs 65. The balls 66 are respectively disposed in a pair of retaining holes 67 formed on the frame 55 and spaced at 180° from each other along the circumferential direction, and are partly projected from the inner surface of the frame 55. The balls 65 are radially and inwardly pressed by the leaf springs 64, respectively. When the slide ring 56 is located at the normal position shown in FIG. 5, the projections 59, disposed in the guide grooves 60 or locking grooves 61, are respectively engaged with the balls 65, thereby restricting the rotation of the slide ring 56. When the position of the slide ring 56 is switched, the slide ring is rotated against the urging force of the leaf springs 64, and the balls 65 are radially pressed out by the projections 59.

On the other hand, the inner periphery of the slide ring 56 thus constructed is formed in an inner diameter large enough to loosely insert the connector 11 of the first type of endoscope 1. An engaging groove 68 is formed as an engaging portion for positioning fixedly the connector 22 of the second type of endoscope 2 at a predetermined position. In other words, the engaging groove 68 is annularly formed, and the elastic engaging ring 30 of the connector 22 is engaged with the groove 68. Further, an annular stopper 69, formed of a stepped part, is formed on the inner surface of the slide ring 56. The peripheral edge of the end plate 26 of the connector 22 is in contact with the stopper 69, when the engaging ring 30 is engaged with the engaging groove 68. The stepped part 28 of the connector 22 is formed to also make contact with the front end of the slide ring 56. The contact pins 35 are exposed from the cylindrical member 51 in such a state that the connector 22 is connected to the socket 44 so as to make contact with second electric connection terminals 70. These contact terminals 70 are mounted on the above-described contact frame 63.

The supporting frame 55 and the contact frame 63 are enclosed by an outer case 72 of a substantially cylindrical shape which projects from the front panel 42 of the light source device 41. The outer case 72 has at its front end an opening 73 of a substantially circular shape coaxial with the socket 44 having a diameter larger than the outer diameter of the connector body 23, and both right and left walls of the front end portion of the outer case are notched to form finger inserting openings 74. The slide ring 56 may be rotated by holding the right and left walls of the slide ring 56 with the fingers. Thus, anti-slip knurls 75 are respectively formed on that portions of the peripheral wall of the slide ring 56 which are opposed to the finger inserting openings 74. The openings 74 are formed also so that the mouthpieces 17, 18, 19, 20 of the connectors 11, 22 may not make contact with the outer case 72. A small circular-arc shaped part 76 is formed on the top of the opening 73 of the outer case 72, and a large circular-arc shaped part 77 is formed on the lower part of the opening. A plurality of guide cutout grooves 78 are respectively formed on the inner edges of the small and large circular-arc shaped parts 76 and 77 so as to insert the contact pins 35 of the second type of connector 22. The second electric connection terminals 70, which make contact with the contact pins 35, are respectively opposed to the guide cutout grooves 78.

An electric circuit section (not shown) is mounted in the space in the large circular-arc shaped part 73, and processes electric signals transmitted and received through the second connection terminals 70 to the endoscope 2. In other words, the superposed signals are individually reproduced, or the individual signals are superposed, thereby matching the electric system between the light source device 41 and the endoscope 2.

In the light source device 41 are provided a photographing drive power source circuit and an exposure control circuit (both not shown), which are connected to the first electric connection terminals 49 and connected to the second electric connection terminals 70 through the matching circuit.

Figure 6:
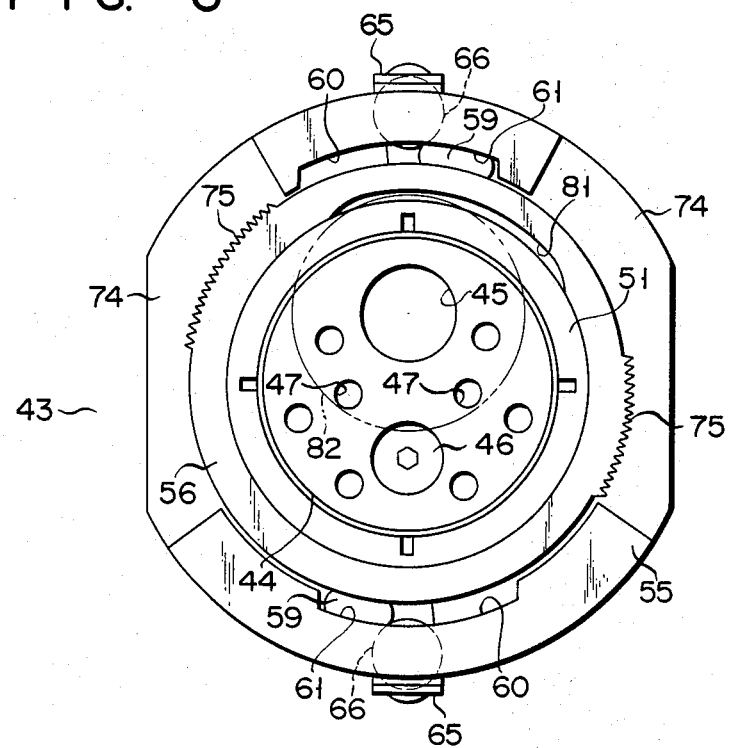

A notched groove 81 are formed, as shown in FIG. 6, on the top of the inner peripheral surface of the front end of the slide ring 56. When the connector 82 of an industrial endoscope having, for example, only a light guide tube is connected to the socket 44, the groove 81 prevents the slide ring 56 from being in contact the outer periphery of the connector body of the connector 82.

Now, the method of using the connecting mechanism 43 constructed as described above will be described. When the connector 11 of the first type of endoscope 1 is connected to the connecting mechanism 43, the connector 11 is inserted through the opening 73 of the outer case 72 thereinto and pressed to plug the light guide tube 14, the gas feeding tube 15 and the contact pins 16 into the light guide tube inserting hole 45, the gas feeding tube inserting hole 46 and the contact pin inserting holes 47. Then, the connector body 12 is introduced through the slide ring 56 and inserted at the end into the engaging gap 53. Then, the engaging ring 21 is engaged with the engaging groove 54 to position the connector 11 at a predetermined position. In other words, the light guide tube 14, the gas feeding tube 15 and the contact pins 16 are inserted at predetermined positions, so that the contact pins 16 are connected to the first electric connection terminal 49, and the gas feeding tube 15 is connected to the gas feeding pipe 48. Thus, the endoscope 1 and the light source device 41 are electrically, optically and hydraulically connected.

On the other hand, when the second type connector 22 of the endoscope 2 is mounted, the slide ring 56 is turned clockwise by the fingers, and the projections 59 are engaged and locked to the locking grooves 58. In other words, the slide ring 56 is disposed in the disabled state to be inserted, and is held at the normal position. Then, the connector 22 is inserted from the opening 73 of the outer case 72, in such a state that the contact pins 35 of the connector 22 are engaged with the corresponding cutout grooves 64. Since the connector body 23 has an outer diameter larger than that of the first type of connector 11, the connector 22 is not introduced into the depth of the cylindrical member 51, but makes contact with the slide ring 56, and the elastic engaging ring 30 is engaged with the engaging groove 68. Since the stepped part 28 of the connector body 23 is in contact with the stopper 69 at this time, the connector is reliably positioned in the inserting direction. The light guide tube 31 and the gas feeding tube 32 are similarly coupled to the socket 44 side. The light guide tube 31 and the gas feeding tube 32 are projected lengthwise to be longer than that of the first type of connector 11, and are accordingly coupled to the socket 44. The contact pins 35 are connected to the second electric connection terminals 70 in this coupled state, and are connected to an electric device in the light source device 41 through the matching circuit as described above.

In the above-described constitution, when the connectors 11, 22 are connected, the contact pins 16, 35 are electrically connected to the light source device 41 side merely by directly contacting the contact pins 16, 35 with the electric connection terminals 49, 70, respectively. Therefore, the electric connection has more electric reliability compared to the conventional type of the connecting machanism in which the electric connection is executed through a plurality of contacts.

As shown by a dotted line in FIG. 5, a connector of another special type (hereafter referred as to "a third type" of connector) is provided in the same structure as the connector 11 except that the connector body 86 has an outer diameter larger than that of the body 23 of the second type of connector 22. The connector body 86 does not pass through the slide ring 56. When this connector 88 is connected to the socket 44 for use, the slide ring 56 is rotated counterclockwise so that the projections 59 are disposed at the guide grooves 60 side. As a result, the slide ring 56 is switched to the state capable of being plugged in. Then, when the third type of connector 88 is inserted through the opening 73 of the outer case 72, the front end of the connector body 86 abuts against the end of the slide ring 56. When the connector 88 is strongly inserted even after the front end of the body 86 makes contact with the outer end of the slide ring 56, the slide ring 56 is introduced by the length l until the stopper 69 makes contact with the front end of the cylindrical member 51, as shown in FIG. 5, while resisting the urging force of the coiled spring 62. In other words, the slide ring 56 is moved by the connector 88 to the evacuating position for allowing the connector 88 of the third type to be connected to the socket 44. Thus, the light guide tube 14 and the gas feeding tube 15 of the connector 88 are respectively inserted into the corresponding holes 45, 46 of the socket 44, and the elastic engaging ring 21 is engaged with the engaging groove 54.

According to the connecting mechanism 43 as described above, the connector of the endoscope of a different type may be simply connected to the socket 44 of one type as it is without utilizing the adapter of other member. Therefore, a complication such as selection and use of the adapters can be eliminated, and the connector may be readily and rapidly connected by arbitrar selection. Further, the adapter of other member is not necessary, so that the cost can be accordingly reduced, and the internal structure of the socket can be simplified.

Further, since one holding means which interferes the connection of the connector adapted to the other holding means is supported in a movable manner to be evacuated, the connector may be coupled to the socket by avoiding the interference of the holding means even when the type of the connector connected to the other holding means is different so that the outer diameter is interfered with the other holding means. Consequently, the connector of this special type can be used and handled in a very convenient manner. In other words, the complication of mounting and dismounting the adapters may be eliminated.

In the embodiments described above, the socket 44 and the cylindrical member 51 may be integrally formed. Moreover, the clicking mechanism 64 may be provided with only one ball 65.

What is claimed is:

1. A connecting mechanism of a light source device for an endoscope to which a various types of connectors of endoscopes are selectively connected; the first type of connector having a substantially cylindrical connector body connected at one end to the endoscope and at the other end having a recess, and at least one electric contact and a light guide tube extended along the axial direction of the connector body from the bottom of the recess; the second type of connector having a substantially cylindrical connector body connected at one end to the endoscope and closed at the other end, said connector body of the second type of connector having a diameter larger than the body of the first type of connector, a light guide tube extended along the axial direction of the body from the other end of the connector body, and at least one electric contact projected from the outer peripheral surface of the connector body; and the third type of connector having a substantially cylindrical connector body connected at one end to the endoscope and having at the other end a recess, said connector body of the third type of the connector having a diameter larger than the body of the second type of connector, and at least one electric contact and a light guide tube extended along the axial direction of the connector body from the bottom of the recess; said connecting mechanism comprising:

a socket having a connecting portion to which the light guide tubes of the various types of connectors and the electric contacts of the first and third types of connectors are connected;

first holding means for engaging with the other end of the connector body of the first type of connector to hold it when the light guide tube and the contacts of the first type of connector are connected to the socket; and second holding means for engaging with the other end of the connector body of the second type of connector to hold it when the light guide tube of the second type of connector is connected to the socket, the second holding means having a contact portion which contacts with the other end of the connector body of the third type of connector, and being arranged to be movable between a normal position for engaging with the connector body of the second type of connector and an evacuating position for allowing the third type of connector to be connected to the socket, and the second holding means being in contact with the connector body of the third type of connector and moved to the evacuating position by the third type of connector when the third type connector is connected to the socket.

2. The connecting mechanism according to claim 1, wherein said socket is mounted on the light source device and has a substantially cylindrical shape, one end thereof being formed to be engagable with the recesses formed on the connector bodies of the first and third types of connectors, said socket has a light guide tube inserting hole and contact inserting holes formed along the axial direction of the socket and opened to one end of the socket to be respectively inserted with the light guide tube and the electric contact.

3. The connecting mechanism according to claim 2, wherein said first holding means has an annular engaging groove formed coaxially with the socket at the outside of one end of the socket and adapted to engage with the other end of the connector body of the first type of connector.

4. The connecting mechanism according to claim 3, wherein said first holding means has a cylindrical member fitted to the outside of the socket, and the cylindrical member has an annular recess defining the engaging groove together with the outer peripheral surface of the one end of the socket.

5. The connecting mechanism according to claim 2, which further comprises a supporting frame mounted on the light source device and supporting the socket, and wherein said second holding means includes an annular slide ring supported by the supporting frame and disposed coaxially with the socket, the slide ring has an engaging groove formed on the inner peripheral surface thereof for engaging with the other end of the connector body of the second type connector, and the slide ring is supported by the supporting frame to be axially movable between the normal position where one end of the slide ring is opposed to one end of the socket and the evacuating position where the slide ring is located outside the socket.

6. The connecting mechanism according to claim 5, wherein said slide ring is formed at the other end thereof with the contact portion, the other end of the connector body of the third type connector is contacted with the contact portion when the third type of connector is connected to the socket to move the slide ring from the normal position thereof to the evacuating position.

7. The connecting mechanism according to claim 6, wherein said second holding means includes control means for controlling the movement of the slide ring.

8. The connecting mechanism according to claim 7, wherein said supporting frame has a substantially cylindrical shape and extends coaxially with the socket, the slide ring has an outer diameter larger than the diameter of the connector body of the second type of connector and is substantially equal to the inner diameter of the supporting frame, and is arranged rotatably and slidably along the axial direction thereof in the supporting frame.

9. The connecting mechanism according to claim 8, wherein said control means has at least one projection projected radially outward from the outer periphery of the slide ring, a guide groove extending along the axial direction formed on the inner surface of the supporting frame and engaged with the projection for guiding the movement of the slide ring between the normal position and the evacuating position, a locking groove formed on the inner surface of the supporting frame to extend circumferentially from the guide groove, the locking groove preventing the slide ring from moving to the evacuating position to hold the slide ring at the normal position when the projection is engaged with the locking groove, and urging means coupled to the slide ring for urging the slide ring toward the normal position.

10. The connecting mechanism according to claim 9, wherein said control means includes a clicking mechanism for positioning the projection of the slide ring in the guide groove or locking groove, the clicking mechanism has a holding hole formed through the supporting frame and opened in the boundary between the guide groove and the locking groove, a locking member arranged in the holding hole to partially project from the inner periphery of the supporting frame and to be in contact with the projection of the slide ring, thereby restricting the rotation of the slide ring, and an urging member mounted on the supporting frame and engaged with the locking member for urging the locking member into the supporting frame.

11. The connecting mechanism according to claim 10, wherein said supporting frame is formed at the position opposed to the slide ring with a finger inserting opening for allowing the slide ring to be operated externally of the supporting frame.

12. The connecting mechanism according to claim 5, which further comprises an electric connection terminal mounted on the supporting frame, disposed in the vicinity of the other end of the slide ring, and adapted to contact with the electric contact of the second type of connector when the second type of connector is connected to the socket.

13. The connecting mechanism according to claim 12, which further comprises an outer case mounted on the light source device to enclose the supporting frame and the electric connection terminal, the outer case has a finger inserting opening for allowing the external operation of the slide ring, and an opening which is formed coaxially with the slide ring, opposed to the other end of the slide ring, and has a diameter larger than the connector body of the third type of connector.

* * * * *